US010861598B2

(12) United States Patent
Pipher et al.

(10) Patent No.: US 10,861,598 B2
(45) Date of Patent: Dec. 8, 2020

(54) HISTORICAL IDENTIFICATION AND ACCURACY COMPENSATION FOR PROBLEM AREAS IN A LOCATING SYSTEM

(71) Applicant: Hill-Rom Services, Inc., Batesville, IN (US)

(72) Inventors: Britten J. Pipher, Raleigh, NC (US); Kenzi L. Mudge, Raleigh, NC (US); Stephen R. Embree, Chapel Hill, NC (US); Brandon M. Ayers, Carrboro, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 16/272,063

(22) Filed: Feb. 11, 2019

(65) Prior Publication Data
US 2019/0252064 A1    Aug. 15, 2019

Related U.S. Application Data

(60) Provisional application No. 62/630,404, filed on Feb. 14, 2018.

(51) Int. Cl.
| G16H 40/20 | (2018.01) |
| G06K 19/077 | (2006.01) |
| A61B 90/98 | (2016.01) |

(52) U.S. Cl.
CPC ........... *G16H 40/20* (2018.01); *A61B 90/98* (2016.02); *G06K 19/07713* (2013.01)

(58) Field of Classification Search
CPC ... A61B 5/115; A61B 5/0002; G08B 21/0446; H04W 56/0015; H04W 56/0065; H04W 4/025; G01S 5/0284; G07C 9/00111
See application file for complete search history.

(56) References Cited

U.S. PATENT DOCUMENTS

| 5,291,399 A | 3/1994 | Chaco |
| 5,465,082 A | 11/1995 | Chaco |
| 5,657,236 A | 8/1997 | Conkright |

(Continued)

FOREIGN PATENT DOCUMENTS

| CA | 2655110 A1 | 3/2008 |
| CN | 101095629 A | 1/2008 |

(Continued)

OTHER PUBLICATIONS

Extended European Search Report for Application No. 19156783.3, dated Jul. 3, 2019, 8 pages.

*Primary Examiner* — Mirza F Alam
(74) *Attorney, Agent, or Firm* — Barnes & Thornburg LLP (57) ABSTRACT

A caregiver location system includes a computer configured to track a location of a caregiver in a healthcare facility. A caregiver identification (ID) tag is worn by a caregiver and has a tag transceiver configured to communicate with a plurality of transceivers. The plurality of transceivers and the computer cooperate to form a locating system that is operable to determine a location of the caregiver ID tag. The computer collects data over time related to a caregiver location within the healthcare facility and determines a problem area within the healthcare facility where a determined caregiver location is inaccurate.

24 Claims, 3 Drawing Sheets

(56) References Cited

U.S. PATENT DOCUMENTS

| | | |
|---|---|---|
| 5,703,786 A | 12/1997 | Conkright |
| 5,760,704 A | 6/1998 | Barton et al. |
| 5,790,114 A | 8/1998 | Geaghan et al. |
| 5,822,544 A | 10/1998 | Chaco et al. |
| 5,850,344 A | 12/1998 | Conkright |
| 5,877,675 A | 3/1999 | Rebstock et al. |
| 6,041,305 A | 3/2000 | Sakurai |
| 6,130,860 A | 10/2000 | Suzuki |
| 6,288,978 B1 | 9/2001 | Suzuki |
| 6,728,341 B1 | 4/2004 | Puchek et al. |
| 6,909,359 B1 | 6/2005 | McGovern |
| 6,911,916 B1 | 6/2005 | Wang et al. |
| 6,957,187 B1 | 10/2005 | Kameda |
| 7,263,669 B2 | 8/2007 | Denholm |
| 7,319,386 B2 | 1/2008 | Collins, Jr. et al. |
| 7,344,079 B2 | 3/2008 | Steusloff et al. |
| 7,357,308 B2 | 4/2008 | Matz |
| 7,364,067 B2 | 4/2008 | Steusloff et al. |
| 7,475,019 B2 | 1/2009 | Rosenfeld et al. |
| 7,522,477 B1 | 4/2009 | Sheldon |
| 7,562,026 B2 | 7/2009 | DelMonego et al. |
| 7,567,238 B2 | 7/2009 | Sugimoto et al. |
| 7,587,329 B2 | 9/2009 | Thompson et al. |
| 7,607,571 B2 | 10/2009 | Steusloff et al. |
| 7,671,733 B2 | 3/2010 | McNeal et al. |
| 7,676,386 B2 | 3/2010 | Stephenson |
| 7,734,476 B2 | 6/2010 | Wildman et al. |
| 7,749,164 B2 | 7/2010 | Davis |
| 7,831,679 B2 | 11/2010 | Apacible et al. |
| 7,849,620 B2 | 12/2010 | Hussey et al. |
| 7,852,208 B2 | 12/2010 | Collins, Jr. et al. |
| 8,077,552 B1 | 12/2011 | Pope et al. |
| 8,094,521 B2 | 1/2012 | Levy |
| 8,224,667 B1 | 7/2012 | Miller et al. |
| 8,224,683 B2 | 7/2012 | Manos |
| 8,571,884 B2 | 10/2013 | Badgett et al. |
| 8,598,995 B2 | 12/2013 | Schuman et al. |
| 8,719,044 B2 | 5/2014 | Hungerford et al. |
| 8,725,526 B2 | 5/2014 | Cobbs et al. |
| 8,775,207 B2 | 7/2014 | Abraham et al. |
| 8,779,924 B2 | 7/2014 | Pesot et al. |
| 8,799,011 B2 | 8/2014 | Wilson et al. |
| 8,942,676 B2 | 1/2015 | Dalton et al. |
| 9,232,040 B2 | 1/2016 | Barash et al. |
| 9,240,120 B2 | 1/2016 | Girardeau et al. |
| 9,300,646 B1 | 3/2016 | Saylor et al. |
| 9,465,916 B2 | 10/2016 | Girardeau et al. |
| 9,517,035 B2 | 12/2016 | Schuman et al. |
| D814,509 S | 4/2018 | Coffman et al. |
| 10,062,042 B1 | 8/2018 | Kelly et al. |
| 10,157,355 B2 | 12/2018 | Johnson et al. |
| 10,157,536 B2 | 12/2018 | Zuckerman et al. |
| 2002/0183979 A1* | 12/2002 | Wildman ............. G06K 7/0008 702/188 |
| 2003/0149598 A1 | 8/2003 | Santoso et al. |
| 2004/0249250 A1 | 12/2004 | McGee et al. |
| 2006/0004605 A1 | 1/2006 | Donoghue et al. |
| 2006/0053035 A1 | 3/2006 | Eisenberg |
| 2006/0149589 A1 | 7/2006 | Wager |
| 2006/0247948 A1 | 11/2006 | Ellis et al. |
| 2007/0016443 A1 | 1/2007 | Wachman et al. |
| 2007/0112610 A1 | 5/2007 | Johnson et al. |
| 2007/0216660 A1 | 9/2007 | Sposato et al. |
| 2008/0082363 A1 | 4/2008 | Habashi |
| 2008/0106374 A1 | 5/2008 | Sharbaugh |
| 2008/0164998 A1 | 7/2008 | Scherpbier et al. |
| 2009/0021486 A1 | 1/2009 | Chaudhri et al. |
| 2009/0043634 A1 | 2/2009 | Tisdale |
| 2009/0094529 A1 | 4/2009 | Gonzalez et al. |
| 2009/0112618 A1 | 4/2009 | Johnson et al. |
| 2009/0125332 A1 | 5/2009 | Martin |
| 2009/0125335 A1 | 5/2009 | Manetta et al. |
| 2009/0125840 A1 | 5/2009 | Squilla et al. |
| 2009/0178004 A1 | 7/2009 | Stoval, III et al. |
| 2009/0182577 A1 | 7/2009 | Squilla et al. |
| 2009/0254365 A1 | 10/2009 | Gravina |
| 2010/0070294 A1 | 3/2010 | Horne et al. |
| 2010/0188230 A1 | 7/2010 | Lindsay |
| 2010/0198622 A1 | 8/2010 | Gajic et al. |
| 2011/0208541 A1 | 8/2011 | Wilson et al. |
| 2011/0225004 A1 | 9/2011 | Loncar |
| 2011/0276343 A1 | 11/2011 | Lagor et al. |
| 2012/0078661 A1 | 3/2012 | Sheldon et al. |
| 2012/0089419 A1 | 4/2012 | Huster et al. |
| 2012/0253836 A1 | 10/2012 | Nolte et al. |
| 2012/0310664 A1 | 12/2012 | Long et al. |
| 2013/0331121 A1* | 12/2013 | Bandyopadhyay ... H04W 64/00 455/456.1 |
| 2014/0266642 A1 | 9/2014 | Girardeau et al. |
| 2015/0100333 A1 | 4/2015 | Fitzgerald et al. |
| 2015/0154379 A1 | 6/2015 | Cvijanovich et al. |
| 2016/0029160 A1* | 1/2016 | Theurer ................. G16Z 99/00 455/456.1 |
| 2017/0213191 A1 | 7/2017 | Pitcher |
| 2017/0287316 A1 | 10/2017 | Wildman et al. |
| 2018/0004384 A1 | 1/2018 | Fitzgerald et al. |
| 2018/0302869 A1* | 10/2018 | Hollar ............... H04W 56/0065 |
| 2019/0082298 A1* | 3/2019 | Good ...................... G16Z 99/00 |

FOREIGN PATENT DOCUMENTS

| | | |
|---|---|---|
| CN | 102203784 A | 9/2011 |
| EP | 1197178 A1 | 4/2002 |
| JP | 3002446 B1 | 1/2000 |
| JP | 3618169 B2 | 2/2005 |
| JP | 3950624 B2 | 8/2007 |
| JP | 5869490 B2 | 2/2016 |
| WO | 9725682 A1 | 7/1997 |
| WO | 9814888 A1 | 4/1998 |
| WO | 03042781 A2 | 5/2003 |
| WO | 2008061833 A1 | 5/2008 |
| WO | 2010091073 A2 | 8/2010 |

* cited by examiner

HISTORICAL IDENTIFICATION AND ACCURACY COMPENSATION FOR PROBLEM AREAS IN A LOCATING SYSTEM

CROSS-REFERENCE TO RELATED APPLICATIONS

The present disclosure claims priority to U.S. Patent Application Ser. No. 62/630,404, filed Feb. 14, 2018 and titled "HISTORICAL IDENTIFICATION AND ACCURACY COMPENSATION FOR PROBLEM AREAS IN A LOCATING SYSTEM," which is incorporated by reference herein in its entirety.

BACKGROUND

The present disclosure relates to locating systems used in healthcare facilities to track the locations of caregivers and particularly, to a system for improving the accuracy of caregiver location detection.

Healthcare facilities generally track the whereabouts of caregivers to determine whether a caregiver has entered a patient room. Also, data related to the caregiver's position in the patient room may assist in determining what care is being provided for a patient. For example, if the patient requires medication, determining that the caregiver is near the patient's IV may assist in determining that the patient is receiving their medication.

However, in real-time locating systems of the healthcare facility, power may be a key constraint to the accuracy of the system. When identification tags are battery powered, it is generally useful to limit the amount of power used by the tag. To allow for an extended battery life, the identification tags may be restricted to only send signals periodically, e.g. once a second. Because the tags are only periodically transmitting, the system may not be able to perform responsive actions in a timely manner, thereby resulting in inaccuracies in detecting the location of the caregiver.

SUMMARY

The present disclosure includes one or more of the features recited in the appended claims and/or the following features which, alone or in any combination, may comprise patentable subject matter.

According to an aspect of the disclosed embodiments, a caregiver location system may include a computer configured to track a location of a caregiver in a healthcare facility. A plurality of transceivers may be mounted at fixed locations throughout the healthcare facility and may be communicatively coupled to the computer. A caregiver identification (ID) tag that may be worn by the caregiver is provided. The caregiver ID tag may have a tag transceiver configured to communicate with the plurality of transceivers. The plurality of transceivers and the computer may cooperate to form a locating system that is operable to determine a location of the caregiver ID tag. The computer may collect data over time related to a caregiver location within the healthcare facility and may determine a problem area within the healthcare facility where a determined caregiver location is inaccurate. A setting of the caregiver location system may be altered to improve the accuracy of determining the caregiver location in the problem area.

In some embodiments, the computer may determine the problem area based on a set of rules stored within a memory of the computer. The set of rules may include determining that a distance of a first location of the caregiver at a first time from a second location of the caregiver at a second time is greater than a predetermined distance. One second may lapse between the first time and the second time. The set of rules may include determining that an obstacle is positioned between a first location of the caregiver at a first time and a second location of the caregiver at a second time. The obstacle may be a wall or a patient support apparatus.

It may be desired that the computer operates a first algorithm to determine the caregiver location. The computer may operate a second algorithm to improve the accuracy of determining the caregiver location if the caregiver is within the problem area. The second algorithm may have a higher accuracy than the first algorithm. The second algorithm may consume more power than the first algorithm.

It may be contemplated that the caregiver location system is altered by increasing a rate at which the tag transceiver transmits to the plurality of transceivers. The caregiver location system may be altered by adding additional transceivers to the plurality of transceivers. The additional transceivers may be added in the problem area.

In some embodiments, a setting of the caregiver location system may be altered in response to the caregiver entering the problem area.

According to another aspect of the disclosed embodiments, a caregiver location system may include a computer configured to track a location of a plurality of caregivers in a healthcare facility. A plurality of transceivers may be mounted at fixed locations throughout the healthcare facility and may be communicatively coupled to the computer. A plurality of caregiver identification (ID) tags may be provided. Each caregiver ID tag may be worn by one of the plurality of caregivers. Each caregiver ID tag may have a tag transceiver configured to communicate with the plurality of transceivers. The plurality of transceivers and the computer may cooperate to form a locating system that is operable to determine a location of each caregiver ID tag. The computer may operate in a first mode to collect data over time related to caregiver locations within the healthcare facility and may determine problem areas within the healthcare facility where a determined caregiver location is inaccurate. The computer may operate in a second mode to improve the accuracy of determining the caregiver location in the problem areas.

Alternatively or additionally, the computer may determine the problem areas based on a set of rules stored within a memory of the computer. The set of rules may include determining that a distance of a first location of a caregiver at a first time from a second location of the caregiver at a second time is greater than a predetermined distance. One second may lapse between the first time and the second time. The set of rules may include determining that an obstacle is positioned between a first location of a caregiver at a first time and a second location of the caregiver at a second time. The obstacle may be a wall or a patient support apparatus.

It may be desired that the computer operates a first algorithm in the first mode to determine the caregiver location. The computer may operate a second algorithm in the second mode to improve the accuracy of determining the caregiver location if the caregiver is within the problem area.

It may be contemplated that each tag transceiver transmits a message at a first rate in the first mode. Each tag transceiver may transmit the message at a second rate in the second mode.

In some embodiments, the computer may operate in the second mode in response to the caregiver entering the problem area.

According to yet another aspect of the disclosed embodiments, a method of improving the accuracy of a caregiver location system may include tracking a location of a caregiver in a healthcare facility with a plurality of transceivers mounted at fixed locations throughout the healthcare facility. The plurality of transceivers may communicate with a computer. The method may also include forming a locating system with the plurality of transceivers and the computer to determine a location of a caregiver ID tag within the healthcare facility based on a signal from a tag transceiver on the caregiver ID tag. The method may also include operating the computer in a first mode to collect data over time related to caregiver locations within the healthcare facility. The method may also include determining problem areas within the healthcare facility where a determined caregiver location is inaccurate. The method may also include operating the computer in a second mode to improve the accuracy of determining the caregiver location in each of the problem areas.

In some embodiments, the method may also include determining the problem areas based on a set of rules stored within a memory of the computer. Determining the problem areas based on a set of rules may include determining that a distance of a first location of a caregiver at a first time from a second location of the caregiver at a second time is greater than a predetermined distance. One second may lapse between the first time and the second time. Determining the problem areas based on a set of rules may include determining that an obstacle is positioned between a first location of a caregiver at a first time and a second location of the caregiver at a second time. The obstacle may be a wall or a patient support apparatus.

Optionally, the method includes operating a first algorithm in the first mode. The method may also include operating a second algorithm in the second mode to improve the accuracy of determining the caregiver location if the caregiver is within the problem area.

It may be desired that the method includes transmitting a message from each tag transceiver at a first rate in the first mode. The method may also include transmitting a message from each tag transceiver at a second rate in the second mode.

In some embodiments, the method includes operating the computer in the second mode in response to the caregiver entering each of the problem areas.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Figure 1:
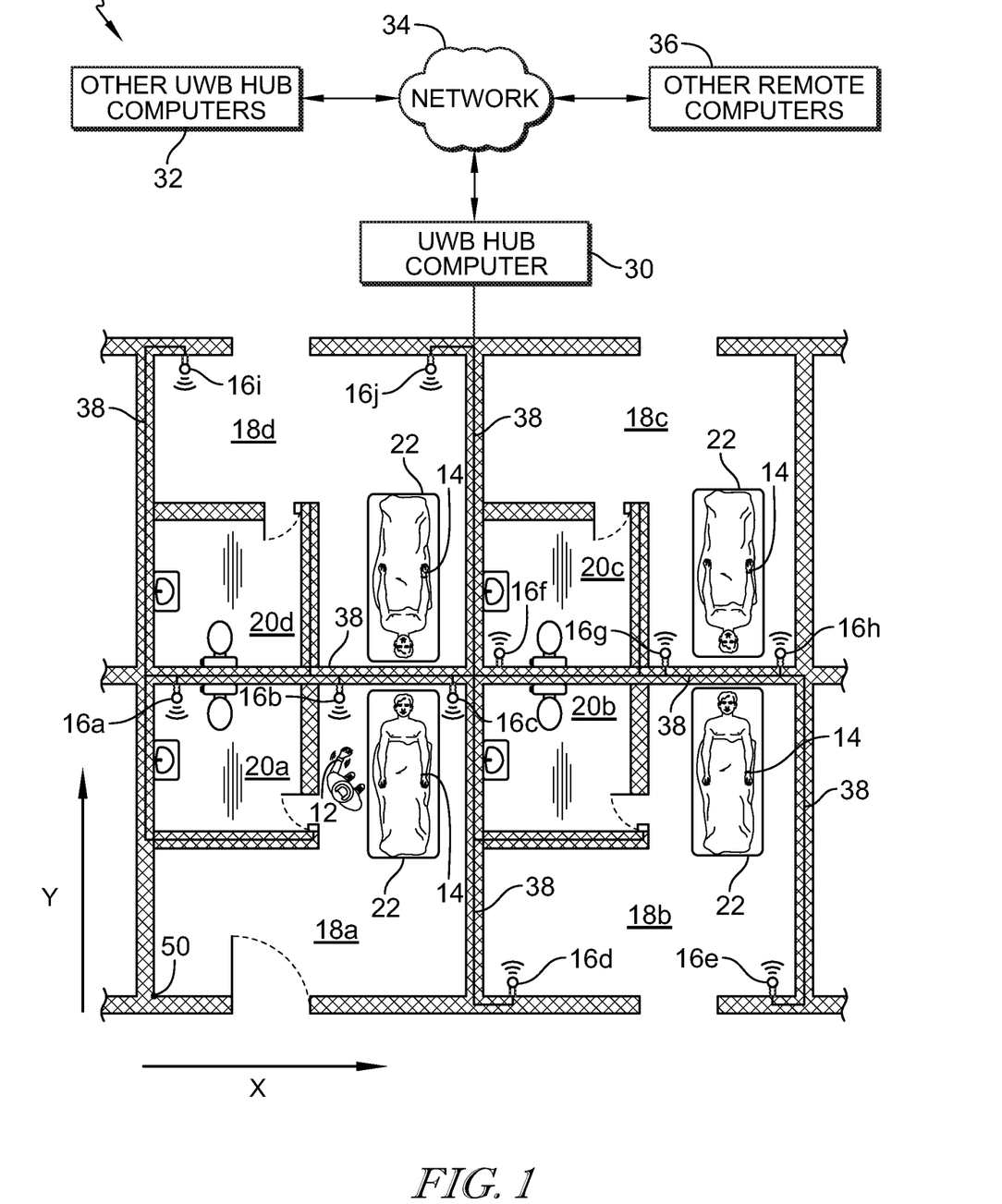
FIG. 1 is a diagrammatic top plan view of patient rooms of a healthcare facility showing a high-accuracy real-time locating system operating to track the locations of caregivers having caregiver identification (ID) tags.

A real-time locating system (RTLS) 10 to track the whereabouts of caregivers and patients in a health care facility such as a hospital or nursing home includes mobile staff tags 12 worn by staff members such as caregivers and housekeepers, and mobile patient tags 14 worn by patients as shown in FIG. 1. System 10 also has a multitude of transceivers, illustratively indicated as transceivers 16*a*-16*j* in FIG. 1. Transceivers 16*a*-16*j* are shown dispersed throughout four patient rooms 18*a*-18*d* located on the same floor of the healthcare facility. Each patient room 18*a*-18*d* has its own bathroom 20*a*-20*d* in the illustrative example. It should be understood that FIG. 1 is a generic representation of a floor plan of a healthcare facility and so other floor plan configurations of patient rooms are, of course, within the scope of the present disclosure.

Tags 12, 14 and transceivers 16*a*-16*j* each include a housing that contains associated circuitry. The circuitry of tags 12, 14 and transceivers 16*a*-16*j* includes for example a processor such as a microprocessor or microcontroller or the like, memory for storing software, and communications circuitry including a transmitter, a receiver and at least one antenna, for example. Tags 12, 14 also include structure to enable attachment to caregivers, patients, and other hospital personnel such as housekeepers. For example, tags 12 may include a necklace so that a caregiver can wear the tag 12 around their neck or may include a clip so that the caregiver can attach the tag 12 to their clothing. Each of tags 14 may include a wristband so that the tags 14 can be worn on the wrists of the associated patients. Transceivers 16*a*-16*j* each include mounting hardware, such as brackets or plates or the like, in some embodiments, to permit the transceivers 16*a*-16*j* to be mounted at fixed locations in the rooms 18*a*-18*d* of the healthcare facility with fasteners such as screws or the like.

Each of rooms 18*a*-18*d* has a patient bed 22 located therein to support a respective patient during their stay in the healthcare facility as shown in FIG. 1. System 10 further includes a hub computer 30 which is communicatively coupled to other hub computers 32 of system 10 via a network 34 of the healthcare facility. In the illustrative example, system 10 is also communicatively coupled to other remote computers 36 of the healthcare facility. Such other remote computers 36 include, for example, nurse call computers, electronic medical records (EMR) computers, admission/discharge/transfer (ADT) computers, a locating server for handling data from hubs 30, 32, and the like.

As shown in FIG. 1, system 10 further includes electrical lines 38 that electrically couple each of transceivers 16*a*-16*j* to hub computer 30. For ease of illustration, the electrical lines 38 are depicted as being routed through the walls of the various rooms 18*a*-18*d*. However, it should be understood that such lines 38 may be routed over a ceiling and/or under a floor of the respective room 18*a*-18*d* at the discretion of the system designer for any given healthcare facility. Transceivers 16*a*-16*j* communicate wirelessly with tags 12, 14 using radio frequency (RF). It is known that RF signals are able to pass through walls, ceilings, floors, and other objects. Thus, according to this disclosure, it is not required that each room 18*a*-18*d* has a transceiver located therein.

According to this disclosure, system 10 operates as a high-accuracy locating system which is able to determine the location of each tag 12, 14 that is in communication with at least three of transceivers 16a-16j within one foot (30.48 cm) or less of the tag's actual location. System 10 is operable to determine the location of tags 12, 14 in 2-dimensional space. One example of a high-accuracy locating system contemplated by this disclosure is an ultra-wideband (UWB) locating system. UWB locating systems operate within the 3.1 gigahertz (GHz) to 10.6 GHz frequency range. Suitable transceivers 16a-16j in this regard include WISER Mesh Antenna Nodes and suitable tags 12, 14 in this regard include Mini tracker tags, all of which are available from Wiser Systems, Inc. of Raleigh, N.C. and marketed as the WISER LOCATOR™ system.

In some embodiments, system 10 uses 2-way ranging, clock synchronization, and time difference of arrival (TDoA) techniques to determine the locations of tags 12, 14 in the X and Y dimensions. See, for example, International Publication No. WO 2017/083353 A1, which is hereby incorporated by reference herein in its entirety for all that it teaches to the extent not inconsistent with the present disclosure which shall control as to any inconsistencies, for a detailed discussion of the use of these techniques in a UWB locating system. Using these techniques, distances between the stationary transceivers 16a-16j and the various mobile tags 12, 14 are determined based on bidirectional wireless signals communicated between tags 12, 14 and transceivers 16a-16j. For example, the distance from each transceiver 16a-16j to any particular tag can be resolved onto the X-Y plane as a circle having a radius equal to the distance and having its center at the particular transceiver 16a-16j. The actual location of the mobile tag 12, 14 is determined based on the point of intersection of three or more of the circles defined by radii from three or more corresponding transceivers 16a-16j.

It should be appreciated that, unless a tag 12, 14 is midway between two transceivers 16a-16j on a straight line connecting the two transceivers 16a-16j (in which case the two circles generated will be tangent to each other at a single point), then two circles that are generated from the two transceivers 16a-16j will intersect at two points such that a circle generated from a third transceiver is needed to determine which of the two points is the one corresponding to the location of the tag 12, 14. Generating fourth, fifth, sixth, etc. circles having other transceivers 16a-16j as their respective centers will further increase the accuracy of determining the actual location of the particular tag 12, 14. Due to small errors introduced by refraction of the RF signal through solid objects, including walls, people, equipment, etc., the three or more circles in many instances will not intersect at exactly the same point and so interpolation between clusters of circle intersections is performed to arrive at the calculated location of the particular mobile tag 12, 14 of interest on the X-Y plane. These considerations are discussed in International Publication No. WO 2017/083353 A1 which is already incorporated by reference herein.

Tracking the locations of multiple mobile tags 12, 14 in substantially real time using 2-way ranging, clock synchronization, TDoA, resolution of circles onto the X-Y plane, and interpolating intersection point clusters of the circles requires a large amount of computational power by hub computers 30, 32 and/or the associated locating server 36. Thus, each hub computer 30, 32 receives incoming data from a predetermined number of transceivers 16a-16j. In the illustrative example of FIG. 1, hub computer 30 receives data from ten transceivers 16a-16j. TDC Acquisition Holdings, Inc. of Huntsville, Ala. which does business as Time Domain, makes a hub computer (referred to as the PLUS Synchronization Distribution Panel) that is capable of receiving incoming data from up to 144 transceivers. The locating server or computer 36, in turn, receives data from the various hubs 30, 32 and tracks or monitors the locations of tags 12, 14 in the healthcare facility.

According to this disclosure, caregiver location data is tracked over time to determine an accuracy of the system 10. If regions of the healthcare facility regularly experience inaccuracies in caregiver detection, the system 10 may be altered to improve accuracy in these regions. For example, additional hardware may be installed within the system 10, including additional transceivers 16 within the problem area or region. In some embodiments, the system 10 may detect when a caregiver is entering a problem area and alter the performance of the system 10. That is, the system 10 may operate in a first mode under normal conditions, and switch to a second mode when the caregiver enters a problem area of the healthcare facility.

In a real-time locating system, greater frequency of locating measurements affords the ability to statistically analyze data and determine measurements such as error variance and accuracy. Having a system which generates measurements many times per second can enable the real-time locating system to do real-time filtering operations such as smoothing, or to take responsive measures to increase system accuracy if position variance is high, such as enabling accuracy enhancing features of the system which would normally be disabled to save power.

The disclosed embodiments collect data from a caregiver or multiple caregivers over time. A statistical analysis is performed in the aggregate data to identify geographic areas (problem areas) which are prone to error. For example, when two subsequent data measurements span a greater distance than the located caregiver would be able to move in the intervening time (or passes through a wall), a reliable mean or median of these two points cannot be determined. However, if this scenario occurs frequently in the same location, the system 10 can flag the problem area and take accuracy-improving measures when a caregiver is entering the problem area.

It should be appreciated that the room geometry and floor plan shown in FIG. 1 is a simplified example for purposes of illustrating the general concept of how one or more of computers 30, 32, 36 are programmed to determine a location of a tag 12, 14. The placement of origin 50 in any given floor plan of any given health care facility is at the discretion of the system programmer and the X, Y coordinate ranges corresponding to patient rooms of any given healthcare facility will vary from facility to facility based on room geometry. In some embodiments, one of transceivers 16a-16j may be chosen as the origin for the X, Y coordinate system if desired.

Figures 2, 3, 4:
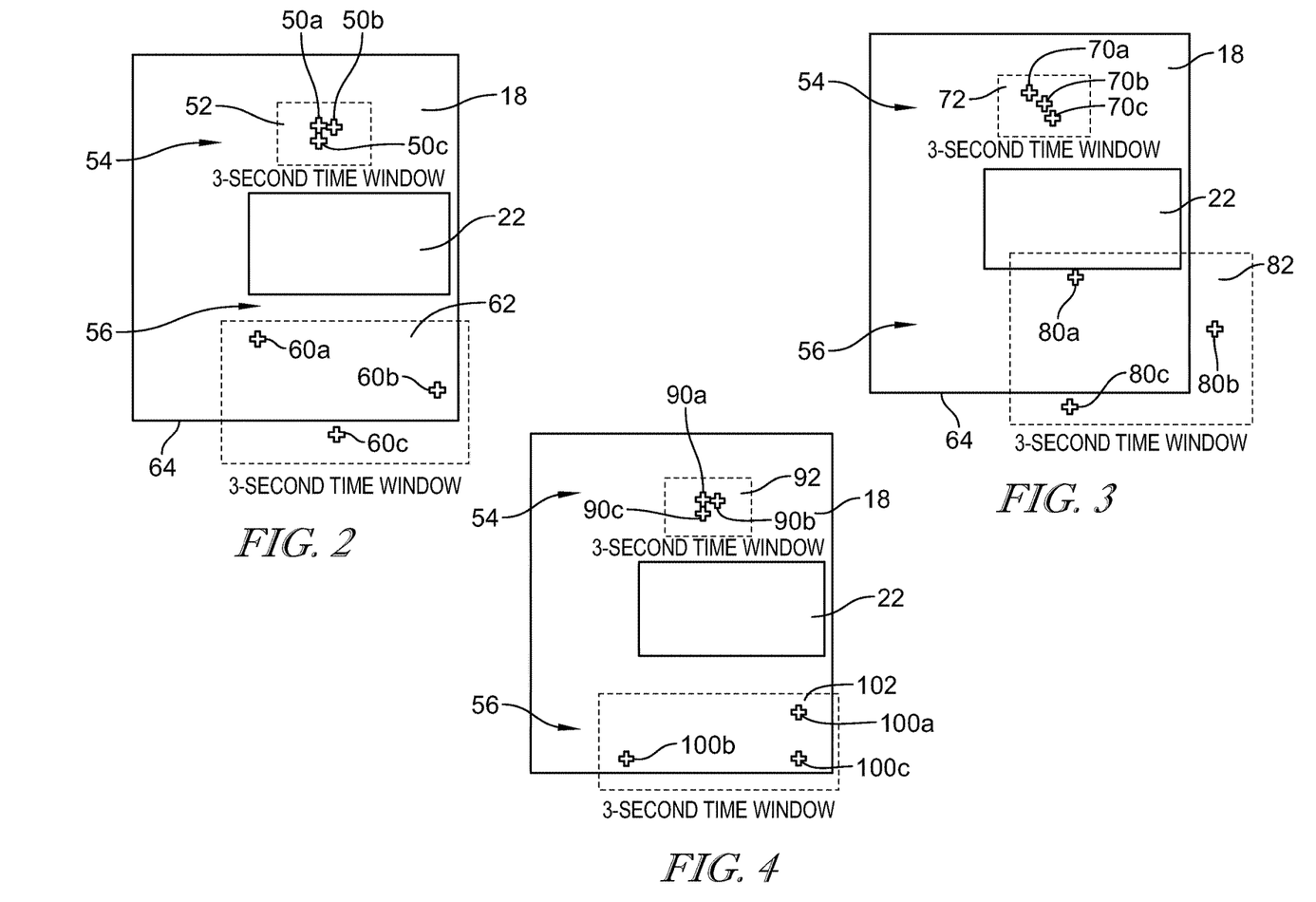
FIG. 2 is a diagrammatic top plan view of a patient room of a healthcare facility showing detected caregiver locations in two regions of the patient room at a first time.
FIG. 3 is a diagrammatic top plan view of the patient room of the healthcare facility showing detected caregiver locations in two regions of the patient room at a second time.
FIG. 4 is a diagrammatic top plan view of the patient room of the healthcare facility showing detected caregiver locations in two regions of the patient room at a third time.

Referring to FIG. 2, caregiver locations as determined by the system 10 are illustrated in a patient room 18 in a first time frame. A first set of caregiver locations 50a-50c is taken in a first region 52 of the patient room 18 on a first side 54 of the patient bed 22. The first set of caregiver locations 50a-50c is taken in a three second window. That is, the first location 50a is taken at a first second, the second location 50b is taken at a second second, and the third location 50c is taken at a third second. As illustrated in FIG. 2, the caregiver locations 50a-c are clustered. The cluster of caregiver locations 50a-50c is indicative of the system 10 having taken accurate measurements of the caregiver's actual location. That is, in three second window, it is logical that the caregiver locations 50a-c would be clustered.

In the first time frame, a second set of caregiver locations 60a-60c is determined by the system 10 in a second region 62 on a second side 56 of the patient bed 22. The caregiver locations 60a-60c are also taken in a three second window. Notably, the caregiver locations 60a-60c are not clustered like the caregiver locations 50a-50c. For example, the caregiver location 60b is detected a significant distance from the caregiver location 60a. The system 10 may determine that given the distance between caregiver locations 60b and 60a, it is unlikely that the caregiver was actually able to move between locations 60b and 60a within one second. Additionally, caregiver location 60c is positioned outside of the patient room 18 on an opposite side of the wall 64. The system 10 may detect these inaccuracies in the caregiver locations 60a-60c and flag the second region 62 as a problem area.

Referring to FIG. 3, caregiver locations as determined by the system 10 are illustrated in the patient room 18 in a second time frame later than the first time frame. A first set of caregiver locations 70a-70c is taken in a first region 72 of the patient room 18. The first set of caregiver locations 70a-70c is taken in a three second window. As illustrated in FIG. 3, the caregiver locations 70a-70c are clustered. The cluster of caregiver locations 70a-70c is indicative of the system 10 having taken accurate measurements of the caregiver's actual location. That is, in three second window, it is logical that the caregiver locations 70a-70c would be clustered.

In the second time frame, a second set of caregiver locations 80a-80c is determined by the system 10 in a second region 82. The caregiver locations 80a-80c are also taken in a three second window. Notably, the caregiver locations 80a-80c are not clustered like the caregiver locations 50a-50c or 70a-70c. Rather, each of the caregiver locations 80a-c are spaced in a manner that the system 10 can conclude that the caregiver could not have actually moved from location 80a to location 80b and then to location 80c. In fact, both locations 80b and 80c were detected past the walls 64 of the room 18.

Referring to FIG. 4, caregiver locations as determined by the system 10 are illustrated in the patient room 18 in a third time frame later than the second time frame. A first set of caregiver locations 90a-90c is taken in a first region 92 of the patient room 18. The first set of caregiver locations 90a-90c is taken in a three second window. As illustrated in FIG. 4, the caregiver locations 90a-90c are clustered. The cluster of caregiver locations 90a-90c is indicative of the system 10 having taken accurate measurements of the caregiver's actual location. That is, in three second window, it is logical that the caregiver locations 90a-90c would be clustered.

In the second time frame, a second set of caregiver locations 100a-100c is determined by the system 10 in a second region 102. The caregiver locations 100a-100c are also taken in a three second window. Notably, the caregiver locations 100a-100c are not clustered like the caregiver locations 50a-50c, 70a-70c, and 90a-90c.

The system 10 collects data over time related to the caregiver locations. Based on the data collected with respect to FIGS. 2-4, the system 10 can determine that second regions 62, 82, and 102 are prone to detecting invalid data and therefore, are problem areas. Because each of these second regions 62, 82, and 102 overlap, the system 10 may flag any area on the second side 56 of the patient bed as a single problem area or a region wherein the system 10 receives inaccurate data regarding the caregiver location.

Figure 5:
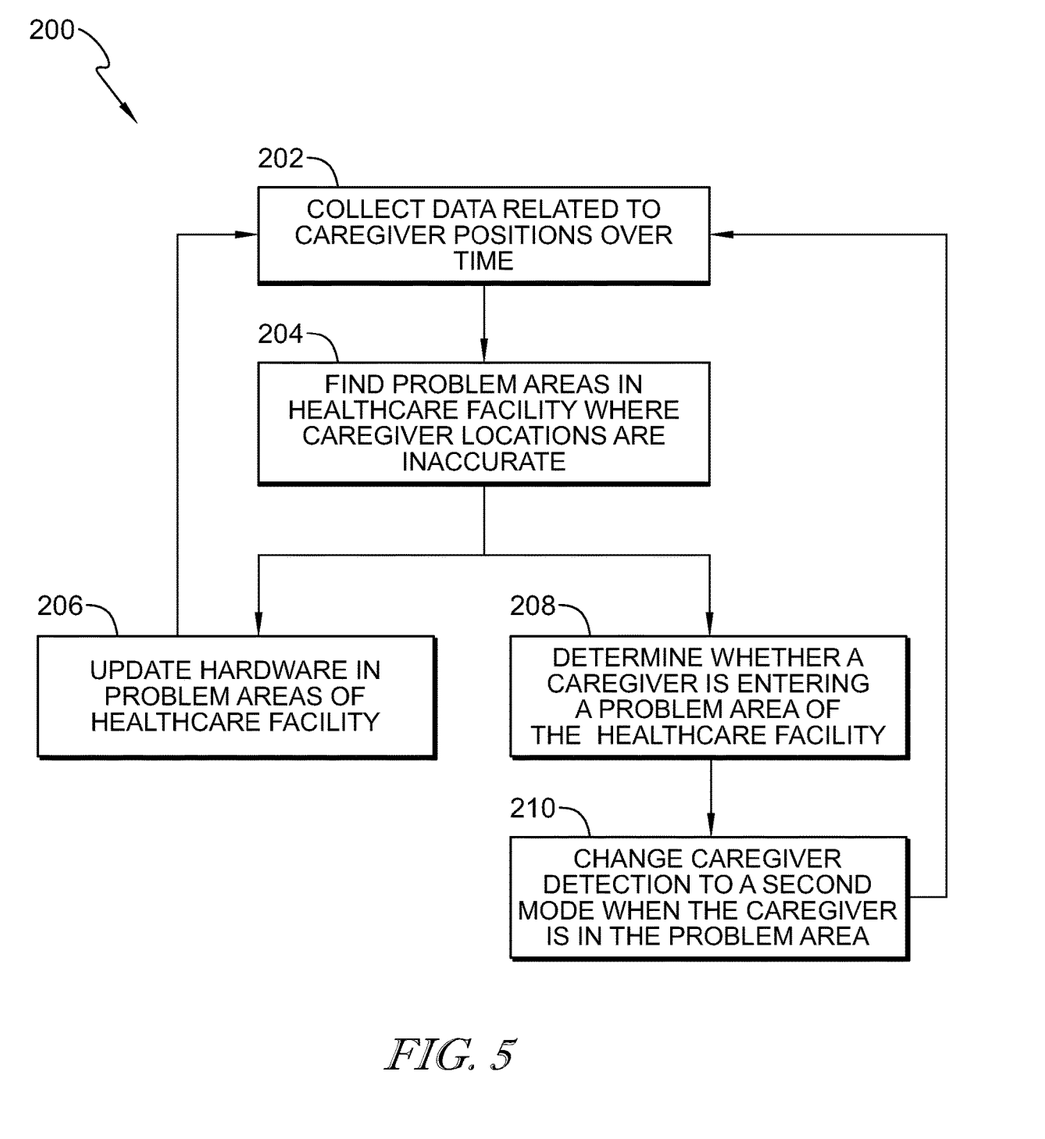
FIG. 5 is a flowchart of a routine for correcting inaccuracies in the detection of caregiver locations.

FIG. 5 illustrates a routine 200 for determining and correcting such inaccuracies. At block 202, the system 10 determines caregiver locations over time as exemplified in FIGS. 2-4. The system 10 may also determine the location of other mobile tags over time, for example, mobile tags worn by patients and housekeeping or mobile tags on medical carts or other movable objects in the healthcare facility. Generally, the system 10 operates in a first mode. The first mode may be a low power, low accuracy mode. That is, the system 10 trades accuracy for power, e.g. to extend a battery life of the mobile staff tags 12. In such an embodiment, the mobile staff tags 12 may transmit a signal to the transceivers 16a-16j every one second. The system 10 collects caregiver position data from a plurality of caregivers so that the total data collect by the system 10 is increased. The more caregivers that the system 10 collects data from, the more accurately the system 10 can detect problem areas, e.g. the second regions 62, 82, and 102 detected in FIGS. 2-4.

In an exemplary embodiment, a mapping of the locating area and walls and doors of the healthcare facility is provided by locating software within the system 10. The locating software then examines an N second window of a small number of measurements, e.g. the caregiver locations 50a-50c, 60a-60c, 70a-70c, 80a-80c, 90a-90c, and 100a-100c. An evaluation is then applied to the region by placing a bounding box around the selected x,y points or drawing a circle whose center is the mean value of the x,y points and whose radius is related to the distance between them. An accuracy "confidence level" is then assigned to the region and the system 10 determines problem areas or regions within the healthcare facility that may be subject to inaccurate caregiver detection.

Several factors may determine whether a particular region is a problem area. A memory of the computer 30 may store a set of rules for determining whether a particular region is a problem area. For example, motion sensor data from the locating badge may be compared to the locating data. If the locating data indicates that the caregiver moved three times in the three second window, but no motion sensor data was detected, a discrepancy may be flagged indicating that a region of inaccuracy may exist. Additionally, the system 10 may look for discontinuities in the caregiver's path from one location to another. Such discontinuities may include obstacles in the caregiver's path, e.g. a patient bed, a monitor, a wall, etc. Discontinuities may also exist when the caregiver is detected as following an erratic path, e.g. zig-zagging, moving back and forth, etc. In some embodiments, the system 10 may detect when a caregiver moves too quickly. For example, the system 10 may determine that the caregiver could not have physically moved from a first detected location to a second detected location in the time between the detection of the two locations. Pacing and jittering may also be detected by the system when it can be assumed that the tracked object is actually staying still (for example a locating tag placed on a stationary device). In some embodiments, the system 10 compares the locating data to other statistical data related to the problem area.

At block 206, the inaccuracies are corrected by updating the system hardware. For example, the low-cost, low-accuracy transceivers 16 may be replaced with higher-cost, higher-accuracy transceivers 16 in the problem area. Alternatively or additionally, additional transceivers 16 may be positioned throughout the problem area. It may be desired in some embodiments to rearrange the hardware in the problem area. The transceivers 16 may be reconfigured to improve signal transmission and reception. Further still, furniture in the problem area may be moved. Furniture may cause an obstruction to the transceiver signals. By rearranging the furniture, the transceiver 16 may better transmit and receive signals to and from the mobile tag 12 in a particular area of a room 18.

At block 208, the system 10 determines whether a caregiver is entering a problem area and at block 210 the system 10 is switched to a second detection mode. It should be noted that the steps 206 and 208 may both be implemented to address a problem area in the health care facility. Through determining "confidence levels" the system 10 may create a floor map with squares or circles corresponding to the region confidences. Then the confidence of any given point on the map may be the average or median of all region confidences containing that point. As a mobile tag's predicted path approaches a point with a confidence below a predetermined threshold, at block 208, the system 10 implements the second detection mode for improved accuracy, at block 210.

In some embodiments, when switching to the second mode, the mobile tag 12 is configured to transmit signals at a faster rate. If the mobile tag 12 is configured to transmit at a rate of one transmission per second in the first mode, in the second mode, the mobile tag 12 may transmit a signal at a rate faster than one transmission per second, for example, one transmission per half second. In some embodiments, the locating software of the system 10 operates a different algorithm in the second mode. The system 10 may switch from a fast algorithm to a more precise algorithm. In some embodiments, the system 10 switches from a low-latency algorithm to a larger averaging/median window algorithm. In some embodiments, the system 10 switches to a more accurate localization method, e.g. a time difference of arrival localization method, a two-way ranging localization method, or an angle of arrival localization method. In some embodiments, the second mode may include switching to a higher broadcast rate or switching a timing topology by dynamically reassigning the nodes responsible for clock synchronization. Further still, the system 10 may raise signal characteristics such as a transmit power or a message length. Alternatively or additionally, the system 10 may apply a stricter positive requirement before indicating entry/exit in the problem area.

After blocks 206 and 210, the problem area's accuracy confidence can be updated over time, at block 202. For example, moving obstacles such as beds or furniture in/out of an area may increase or decrease accuracy. This also helps to limit the computational and storage burdens on the system 10 by discarding sufficiently old data.

Although the embodiments are described with respect to a real-time locating system capable of producing x,y measurements, the embodiments could be applied to zone-based real-time locating systems. For instance, if the system 10 puts a tag in rapid alternation between adjacent rooms in such a way that would be very improbable in reality (e.g. if an infrared signal bounces through a window), then the system 10 can take note and apply accuracy enhancing measures as described above in this disclosure.

Although this disclosure refers to specific embodiments, it will be understood by those skilled in the art that various changes in form and detail may be made without departing from the subject matter set forth in the accompanying claims.

The invention claimed is:

1. A caregiver location system comprising:
   a computer configured to track a location of a caregiver in a healthcare facility,
   a plurality of transceivers mounted at fixed locations throughout the healthcare facility and communicatively coupled to the computer, and
   a caregiver identification (ID) tag that is worn by the caregiver, the caregiver ID tag having a tag transceiver configured to communicate with the plurality of transceivers, wherein the plurality of transceivers and the computer cooperate to form a locating system that is operable to determine a location of the caregiver ID tag, wherein the computer collects data over time related to a caregiver location within the healthcare facility and determines a problem area within the healthcare facility where a determined caregiver location is inaccurate, wherein a setting of the caregiver location system is altered to improve the accuracy of determining the caregiver location in the problem area,
   wherein the computer operates a first algorithm to determine the caregiver location using a detecting transceiver of the plurality of transceivers, and wherein the computer operates a second algorithm to improve the accuracy of determining the caregiver location using the detecting transceiver of the plurality of transceivers if the caregiver is within the problem area, wherein the computer does not operate the second algorithm if the caregiver is not within the problem area.

2. The caregiver location system of claim 1, wherein the computer determines the problem area based on a set of rules stored within a memory of the computer.

3. The caregiver location system of claim 2, wherein the set of rules includes determining that a distance of a first location of the caregiver at a first time from a second location of the caregiver at a second time is greater than a predetermined distance.

4. The caregiver location system of claim 3, wherein one second lapses between the first time and the second time.

5. The caregiver location system of claim 2, wherein the set of rules includes determining that an obstacle is positioned between a first location of the caregiver at a first time and a second location of the caregiver at a second time.

6. The caregiver location system of claim 5, wherein the obstacle is a wall.

7. The caregiver location system of claim 5, wherein the obstacle is a patient support apparatus.

8. The caregiver location system of claim 1, wherein the second algorithm has a higher accuracy than the first algorithm.

9. The caregiver location system of claim 1, wherein the second algorithm consumes more power than the first algorithm.

10. The caregiver location system of claim 1, wherein the caregiver location system is altered by increasing a rate at which the tag transceiver transmits to the plurality of transceivers.

11. The caregiver location system of claim 1, wherein the caregiver location system is altered by adding additional transceivers to the plurality of transceivers.

12. The caregiver location system of claim 11, wherein the additional transceivers are added in the problem area.

13. The caregiver location system of claim 1, wherein a setting of the caregiver location system is altered in response to the caregiver entering the problem area.

14. A caregiver location system comprising:
   a computer configured to track a location of a plurality of caregivers in a healthcare facility, a plurality of transceivers mounted at fixed locations throughout the healthcare facility and communicatively coupled to the computer, and a plurality of caregiver identification (ID) tags, each caregiver ID tag worn by one of the plurality of caregivers, each caregiver ID tag having a tag transceiver configured to communicate with the plurality of transceivers, wherein the plurality of transceivers and the computer cooperate to form a locating system that is operable to determine a location of each caregiver ID tag, wherein the computer operates in a first mode to collect data over time related to caregiver locations within the healthcare facility and determines problem areas within the healthcare facility where a determined caregiver location is inaccurate, wherein the computer operates in a second mode to improve the accuracy of determining the caregiver location in each of the problem areas, wherein the computer operates a first algorithm in the first mode to determine the caregiver location using a detecting transceiver of the plurality of transceivers, and wherein the computer operates a second algorithm in the second mode to improve the accuracy of determining the caregiver location using the detecting transceiver of the plurality of transceivers if the caregiver is within the problem area, wherein the computer does not operate the second algorithm if the caregiver is not within the problem area.

15. The caregiver location system of claim 14, wherein the computer determines the problem areas based on a set of rules stored within a memory of the computer.

16. The caregiver location system of claim 15, wherein the set of rules includes determining that a distance of a first location of a caregiver at a first time from a second location of the caregiver at a second time is greater than a predetermined distance.

17. The caregiver location system of claim 16, wherein one second lapses between the first time and the second time.

18. The caregiver location system of claim 15, wherein the set of rules includes determining that an obstacle is positioned between a first location of a caregiver at a first time and a second location of the caregiver at a second time.

19. The caregiver location system of claim 18, wherein the obstacle is a wall.

20. The caregiver location system of claim 18, wherein the obstacle is a patient support apparatus.

21. The caregiver location system of claim 14, wherein the second algorithm has a higher accuracy than the first algorithm.

22. The caregiver location system of claim 14, wherein the second algorithm consumes more power than the first algorithm.

23. The caregiver location system of claim 14, wherein each tag transceiver transmits a message at a first rate in the first mode, and each tag transceiver transmits the message at a second rate in the second mode.

24. The caregiver location system of claim 14, wherein the computer operates in the second mode in response to the caregiver entering each of the problem areas.

* * * * *